United States Patent [19]

Janzen

[11] Patent Number: 5,437,631
[45] Date of Patent: Aug. 1, 1995

[54] PERCUTANEOUS INTRODUCER SET AND METHOD FOR SEALING PUNCTURE WOUNDS

[75] Inventor: Ernst Janzen, Laren, Netherlands

[73] Assignee: Datascope Investment Corp., Montvale, N.J.

[21] Appl. No.: 58,358

[22] Filed: May 10, 1993

Related U.S. Application Data

[63] Continuation-in-part of Ser. No. 746,339, Aug. 16, 1991, Pat. No. 5,391,183, which is a continuation-in-part of Ser. No. 634,478, Dec. 27, 1990, abandoned.

[51] Int. Cl.$^6$ .................................... A61M 31/00
[52] U.S. Cl. ................................. 604/49; 604/57; 604/73; 128/898; 606/213; 606/214
[58] Field of Search ................... 606/213–217, 606/229, 230; 604/11, 13–16, 46, 47–49, 57, 59, 61, 64, 73; 128/898

[56] References Cited

U.S. PATENT DOCUMENTS

| | | | |
|---|---|---|---|
| 4,838,280 | 6/1989 | Haaga | 128/751 |
| 5,290,310 | 3/1994 | Makower et al. | 606/213 |

FOREIGN PATENT DOCUMENTS

| | | | |
|---|---|---|---|
| 0476178 | 3/1992 | European Pat. Off. | 606/213 |
| 9222252 | 12/1992 | WIPO | 606/213 |

Primary Examiner—C. Fred Rosenbaum
Assistant Examiner—Ronald K. Stright, Jr.
Attorney, Agent, or Firm—Fitzpatrick, Cella, Harper & Scinto

[57] ABSTRACT

The present invention relates to an improved device for inserting collagen or other hemostatic materials into a puncture wound made during a percutaneous procedure. The device permits precise location of the collagen relative to the artery wall and also enables insertion of the collagen at the outset of the percutaneous procedure, when the area is anaesthetized.

7 Claims, 6 Drawing Sheets

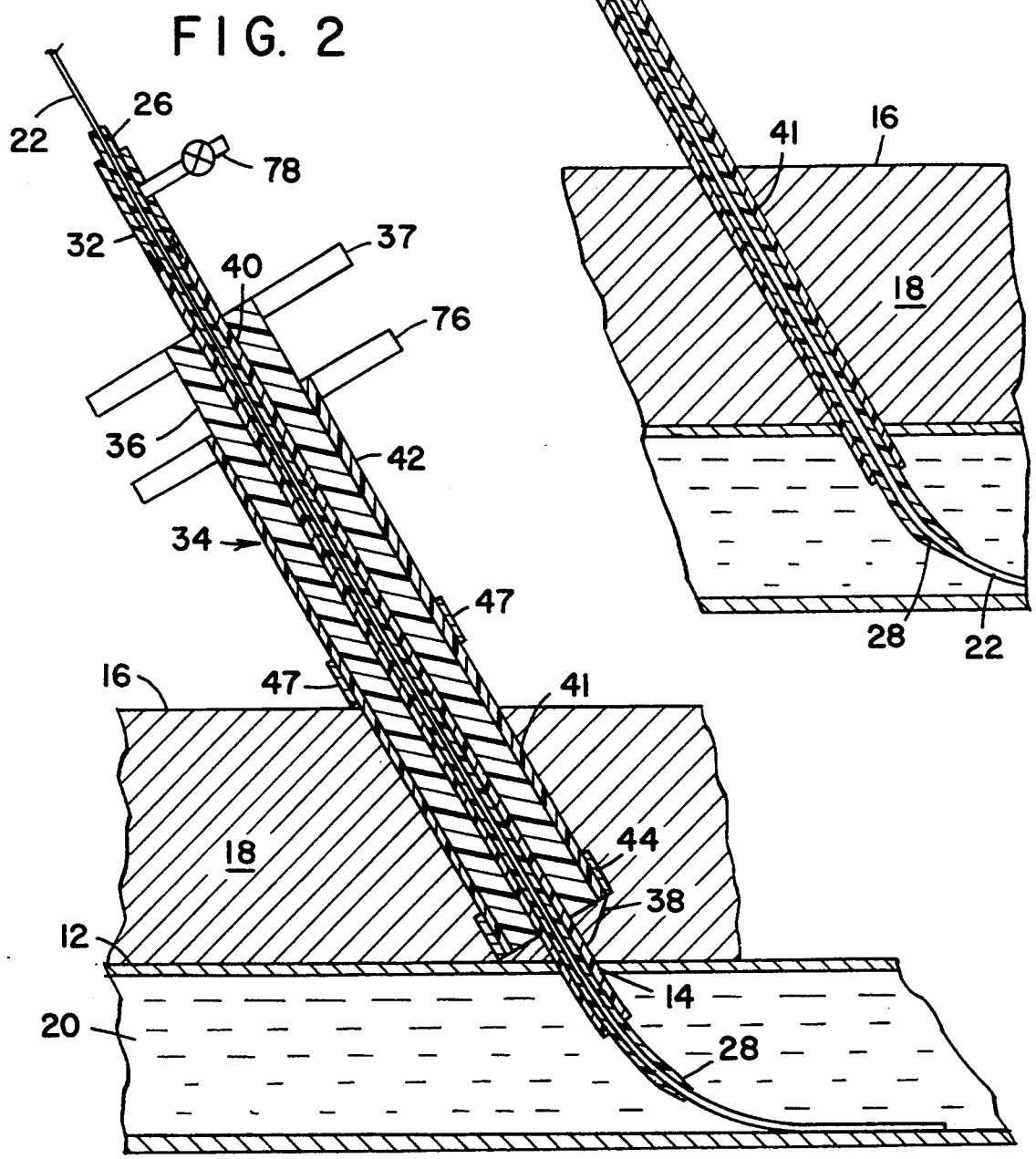

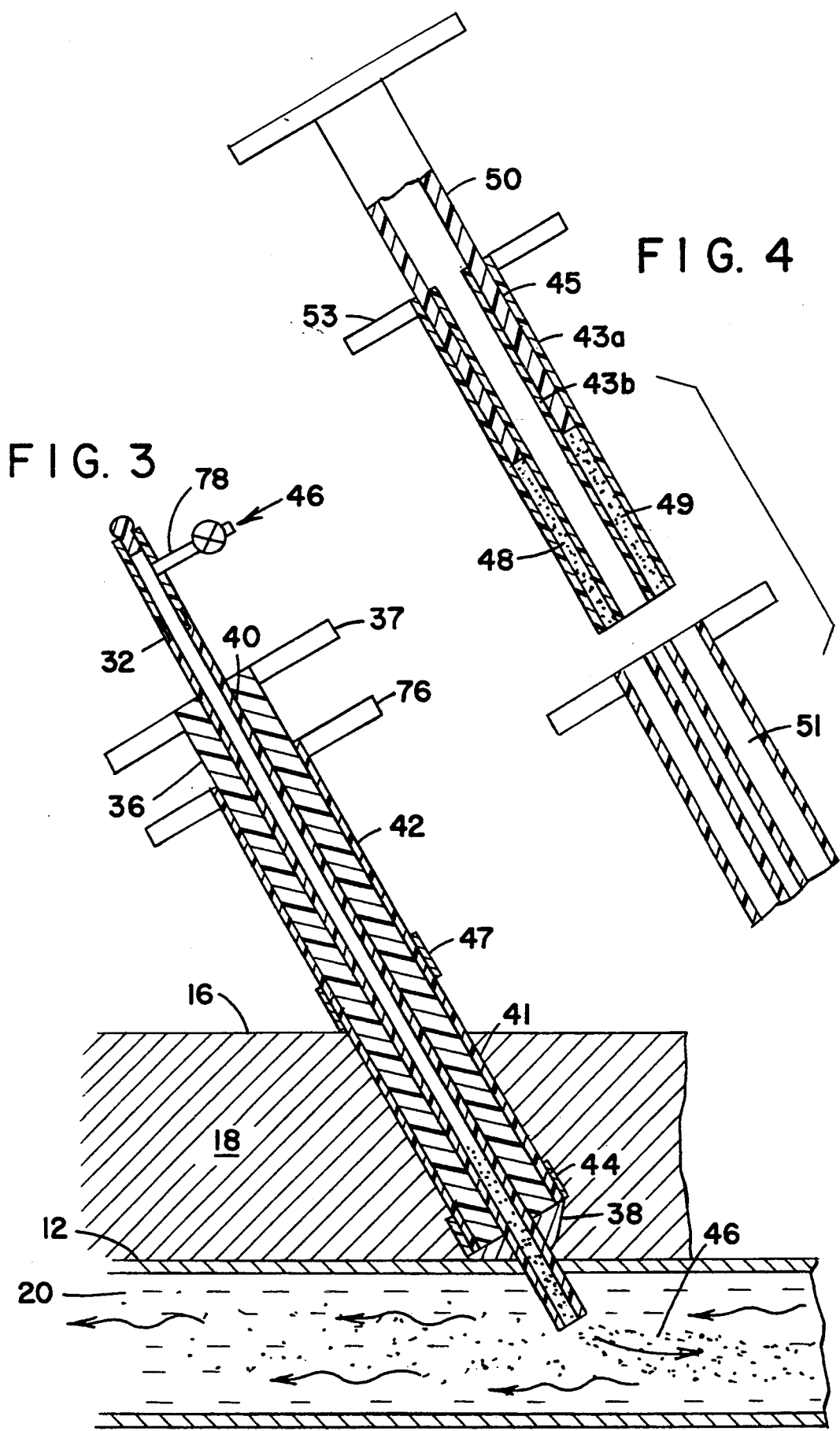

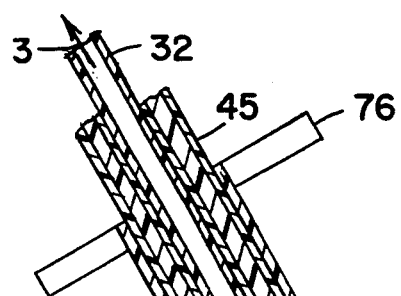
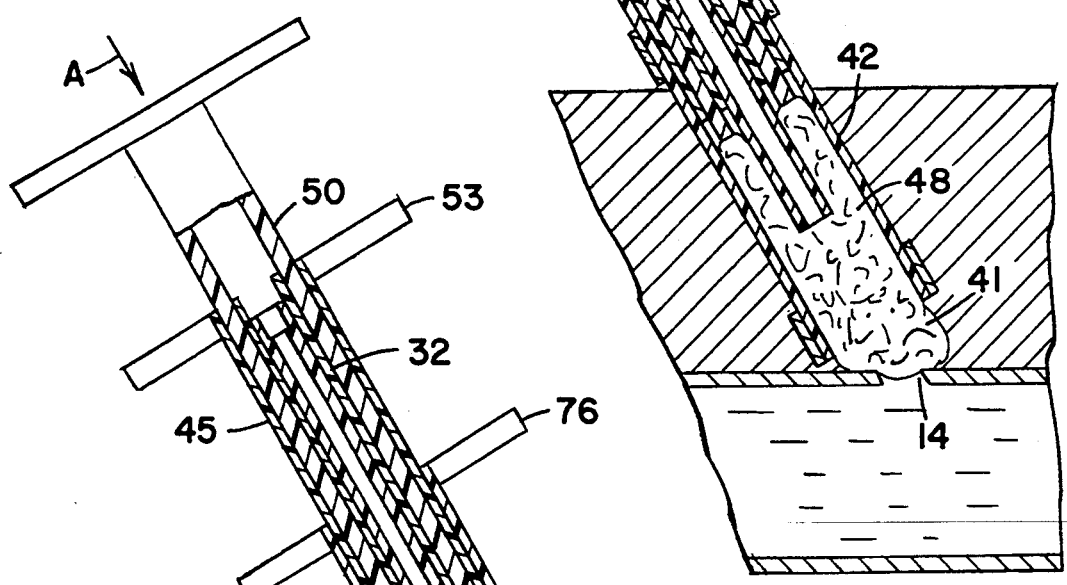
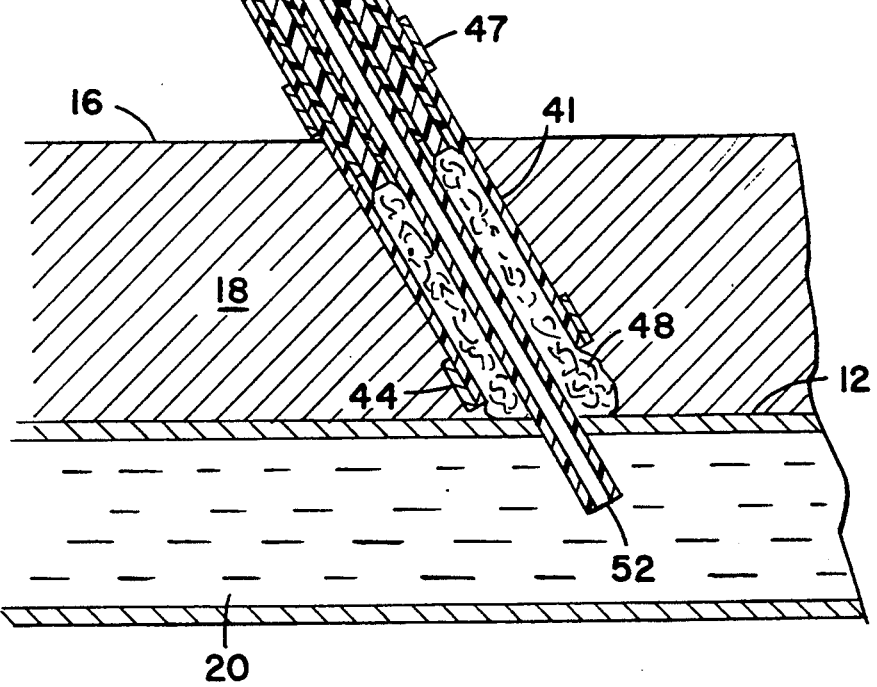

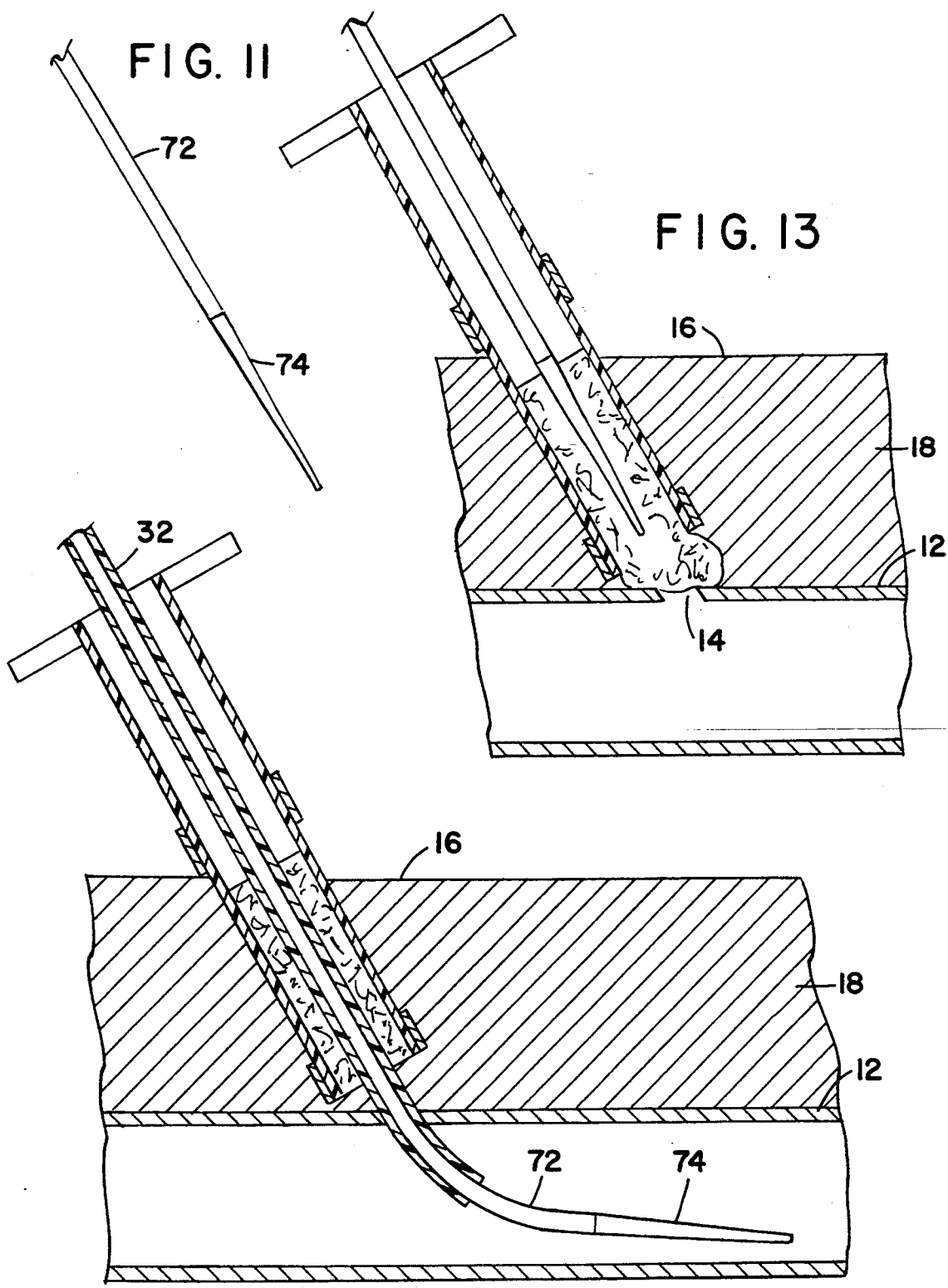

PERCUTANEOUS INTRODUCER SET AND METHOD FOR SEALING PUNCTURE WOUNDS

RELATED APPLICATIONS

The present application is a continuation-in-part of application Ser. No. 7/746,339 filed Aug. 16, 1991, now U.S. Pat. No. 5,391,183, which is itself a continuation-in-part of application Ser. No. 7/634,478 filed Dec. 27, 1990, now abandoned.

BACKGROUND OF THE INVENTION

1. Field of the Invention

The present invention relates to a method for sealing a puncture wound in a blood vessel and a device in the nature of an introducer set for practicing said method.

2. Related Background

In certain medical procedures, such as cardiac catheterization, dilatation and counterpulsation, a catheter or other device is inserted into an artery, most commonly by percutaneous methods, and then fed through the arterial system to the site where needed, frequently, the region of the heart. The site usually selected for insertion is the groin, because the femoral artery in that region is relatively easy to locate.

These procedures are normally initiated by insertion of an angiographic needle, followed by passing a guide wire through that needle into the artery. The needle is then removed leaving the guide wire in place. Next, a sheath-dilator introducer set is passed over the guide wire into the artery in order to enlarge the opening sufficiently to permit entry of the catheter or other device. The dilator of the introducer set is then removed, leaving the sheath or guide cannula in place. The catheter or other device can then be inserted through the sheath with full confidence that when it emerges from the distal end it will be within the lumen of the artery.

It should be understood that the subject invention is independent of the nature of the medical device being used to treat the patient. Accordingly, the term "catheter" will be used here in a very generic and broad way to include not only "catheters" in the strict sense, but any device that is inserted into a blood vessel of the body.

Similarly, the subject invention is independent of the blood vessel involved. While it is anticipated that the femoral artery will be the most commonly used blood vessel, other arteries as well as veins might just as easily be involved.

After a procedure, for example, counterpulsation, has been completed, the sheath must be removed and the wound closed. Often, this can be accomplished simply by the use of a pressure dressing, perhaps augmented by the application of digital pressure. Customarily, pressure must be applied for at least 30 minutes, and frequently for much longer than that. While pressure dressings often suffice, it is not uncommon for additional devices, such as sandbags, to be needed. In addition, during this period the patient must be immobilized, lest movement interfere with the closing process. Because of the pressure required, the time during which it must be applied and the need for immobilization, the procedure can be very uncomfortable, even painful. It also requires prolonged personal attention of a health care professional. Finally, wound closures accomplished in this manner are prone to reopen unexpectedly long after closure appears to have been completed. Patients are therefore often required to remain in the hospital for 24 hours or longer.

Because sealing can be such a problem, cardiologists tend to use the smallest calibre catheters when performing catheterization procedures. Larger calibre catheters, however, are far preferable. An improved sealing procedure whereby larger catheters can be used without increasing the sealing difficulties would greatly facilitate cardiac catheterization.

A series of related devices which were designed to address some of these problems is described in U.S. Pat. Nos. 4,744,364, 4,852,568 and 4,890,612. These three patents describe a mushroom or umbrella shaped device which is used to seal the artery from the inside. The head of the device is placed within the arterial lumen and means are provided to pull and hold the underside of the head against the inside wall of the lumen. It is believed, however, that sealing from the inside can be the source of its own problems, including the promotion of clot formation.

Another method for sealing a puncture wound is described in U.S. Pat. No. 4,929,246. The approach taken there is to insert a balloon-tipped catheter into the tissue wound, inflate the balloon against the outside of the hole in the artery and then use a laser to thermally weld the artery closed.

Another approach which uses a balloon-tipped catheter is shown in U.S. Pat. No. 5,108,421. This patent teaches inserting the balloon inside the artery, inflating the balloon and pulling and holding it against the inside of the artery wall while a collagen sponge plug is inserted until it hits the balloon membrane.

The parent applications (Ser. Nos. 07/746,339, now U.S. Pat. No. 5,391,183 and 07/634,478 now abandoned) from which the present application is a continuation-in-part, teach yet a different approach. They teach enlarging the wound channel so it is larger than the puncture in the artery, then inserting a plug of hemostatic material that is itself larger than the arterial puncture wound so that it abuts the arterial wall around the puncture site.

The present invention discloses a new device and method for inserting hemostatic material around and across the arterial puncture so that sealing is done from the outside.

SUMMARY OF THE INVENTION

When using hemostatic plugs to close wounds made during percutaneous procedures, it is important to place the plugs outside of the artery. The present invention describes and claims a new device and method for locating the plugs in the wound channel, but outside of the arterial lumen, and for doing so without inserting anything in the arterial lumen that could interfere with the flow of blood.

In the practice of the present invention, a standard introducer set is used, in accordance with well known techniques, to gain access to a patient's artery. A hollow needle is inserted percutaneously into the artery. A guide wire is then passed through the needle, and the needle is removed. A sheath-dilator set is then passed over the guide wire to enlarge the wound and pass the sheath into the artery.

While the sheath, reinforced by the dilator is in the artery, a second sheath dilator combination is inserted. This one has a blunt-nosed dilator with a large bore lumen adequate to pass over the previously inserted sheath. The blunt nose of the second dilator is made of a radiopaque material. In addition, the front end of the second sheath may also be radiopaque.

When the second sheath-dilator set is inserted, because it has a blunt nose, it will not enter the artery. Rather, it will come to rest against the outside of the artery wall. This can be confirmed by injecting radiopaque contrast medium through the inner sheath. Such contrast medium makes the artery easily visible under fluoroscopy. Accordingly, the physician can easily see the artery wall and, because the front end of the second sheath-dilator set is similarly visible under fluoroscopy, (s)he can make certain that the latter is at the artery wall—not in the arterial lumen and not too far away from the wall.

With the present invention, not only can the physician definitively determine, at the outset of the procedure, that the outer sheath is properly positioned, (s)he can confirm that it is still properly positioned after the angioplasty or angiography or other procedure has been completed. After the procedure, but prior to removal of the inner sheath, contrast medium and fluoroscopy can again be employed to make sure that the outer sheath has not been displaced and is still at the outside of the artery wall.

After having again confirmed the position of the front of the outer sheath, the physician is ready to insert wound-closing hemostatic material. According to the present invention, this can be done in any one of at least three ways, or even by using a combination of these. First, the inner sheath can be withdrawn and one or more collagen plugs can be inserted through the outer sheath, either with or without a guide wire. Second, before withdrawal of the inner sheath, hemostatic material can be inserted into the annular space between the two sheaths. Then, while a plunger urges the hemostatic material forward, the inner sheath is withdrawn. The collagen from the annular space can then close in front of the withdrawing inner sheath. Third, hemostatic material can be inserted into the annular space between the sheaths at the beginning of the procedure. This parked hemostatic material is then available immediately after the medical procedure has been completed.

DESCRIPTION OF THE DRAWINGS

FIG. 1 is schematic sectional view showing a standard sheath dilator introducer set having been inserted into a patient's femoral artery.

FIG. 2 is a schematic sectional view showing a second, blunt nosed sheath dilator inserted over the first sheath dilator set, in accordance with the present invention.

FIG. 3 is a schematic view in section similar to FIG. 2 except that the inner dilator has been withdrawn and contrast medium is in the process of being injected.

FIG. 4 is a schematic view in section showing an insertion sleeve preloaded with hemostatic material and a plunger for pushing the hemostatic material out of the front end of the sleeve.

FIG. 5 is a schematic view in section showing only the inner and outer sheaths in place, both dilators having been withdrawn and hemostatic material having been inserted between the two sheaths through use of the sleeve depicted in FIG. 4.

FIG. 6 is a schematic view in section similar to FIG. 4, except that the inner sheath is in the process of being withdrawn.

FIG. 11 is a schematic side view of a long taper dilator for use in the practice of an alternative embodiment of the present invention.

FIG. 12 is a schematic view in section similar to FIG. 10 with the long-taper dilator of FIG. 11 having been inserted through the inner sheath.

FIG. 13 is a schematic view in section similar to FIG. 12 except that the inner sheath has been completely withdrawn and the long-taper dilator has been partially withdrawn.

DETAILED DESCRIPTION

Figure 7:
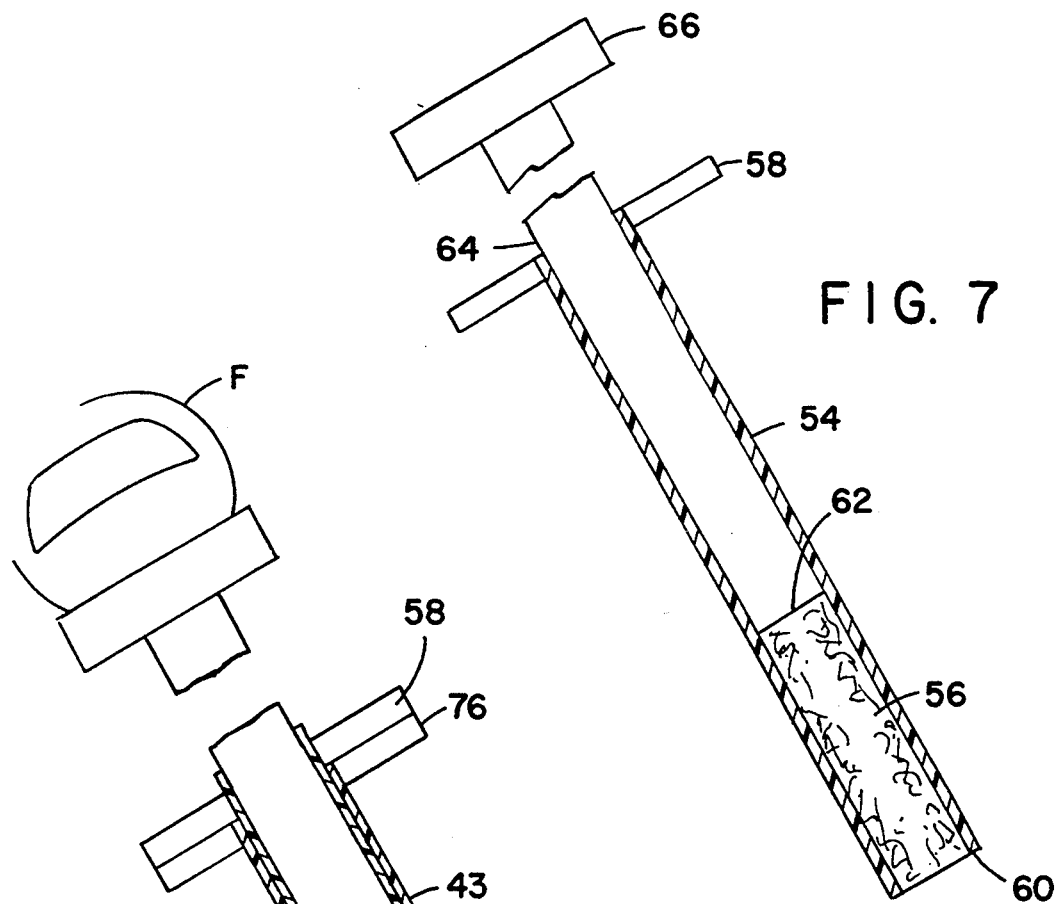
FIG. 7 is a schematic view in section of an alternative embodiment of a preloaded sleeve and plunger.

In certain procedures, for example, intra-aortic balloon pumping ("IABP"), percutaneous transluminal coronary angioplasty ("PTCA") and angiography, a catheter or other device is inserted, often over a guide wire, through a sheath or guide cannula into an artery, most frequently, the common femoral artery in the groin area of the patient's leg. When the procedure (e.g., angioplasty) has been completed, the device (e.g., the balloon catheter), the guide wire and the procedure sheath must be removed and the wound closed.

In accordance with the instant invention, wounds of this type are closed by applying an hemostatic material against the outside of the artery wall 12 over the arterial puncture 14 for a short period of time until a good self-sustaining hemostatic seal is established.

Normally, the medical procedure is initiated by anaesthetizing the groin area using a local anaesthetic such as lidocaine. A hollow needle (not shown) is then inserted percutaneously through the patient's skin 16, through the subcutaneous tissue 18 and into the lumen 20 of the femoral artery. After a guide wire 22 has been passed through the needle, the needle is withdrawn and discarded.

In order to enlarge the wound, a sheath dilator introducer set 24 is passed over the guide wire and into lumen 20 of the artery (see FIG. 1). The sheath dilator set is comprised of a sheath 32 and a dilator 26 that has a taper 28. Sheath 32 may be provided with a side port 78 adapted for receiving a syringe (not shown).

In accordance with the present invention, a second sheath dilator set 34 is then passed over the outside of the first sheath dilator set 24 to further enlarge tissue channel 41. The second sheath dilator set is comprised of a second dilator 36 and a second sheath 42. The second dilator 36 has a radiopaque blunt nose 38, a large bore lumen 40 and may be provided with radially extending wings 37. The bore of lumen 40 is of such size and configuration as to permit dilator 36 to slide over sheath 32. Sheath 42 may be provided with finger lobes 76 and an enlarged collar section 47 to limit the depth to which sheath 42 can be inserted into the wound. In addition, sheath 42 may be provided with a radiopaque band 44 at its distal end.

Due to the size of the second sheath dilator set 34, a slight twisting action may be needed during its insertion. Since, however, at this early stage of the procedure the local anaesthetic is at its maximum effectiveness, the patient should not suffer significant additional discomfort. Since entry of blunt nose 38 into the arterial puncture is, as a practical matter, virtually impossible, the physician has no difficulty determining, simply by tactile sensation, when the front end of the outer sheath dilator set has reached artery wall 12. Alternatively, a sheath may be employed wherein the distance from collar 47 to the distal tip of the sheath is equal to or just slightly shorter than the distance between the puncture through the skin and the puncture through the artery. A method for determining this distance is disclosed in application Ser. No. 7/746,339 now U.S. Pat. No. 5,391,183.

According to one method of practicing the present invention, as depicted in FIG. 3, the first or inner dilator 26 is removed together with the guide wire 22, and contrast medium 46 is injected through side port 78 of sheath 32 into lumen 20. The contrast medium disperses through the blood flowing in the lumen and makes the artery clearly visible under fluoroscopy. Since blunt nose 38 and band 44 are also visible under fluoroscopy, the physician can readily confirm that dilator 36 and sheath 42 are properly positioned with respect to artery 12.

Having thus been assured that the outer sheath is in place, the physician can then proceed with the medical procedure, be it angioplasty, angiography, counterpulsation or the like. When the procedure is completed, dilator 36 can be removed, a preloaded sleeve 45 like that depicted in FIG. 4 can be used to insert hemostatic material 48, preferably in the form of fibrous collagen, into the annular space 51 between the inner and outer sheaths. Preloaded sleeve 45 has coaxial cylinders 43a and 43b which define an annular space 49 into which hemostatic material 48 is preloaded and wings 53. Seated in annular space 49 behind hemostatic material 48 is pusher 50. As depicted in FIG. 5, after removal of blunt dilator 36, sleeve 45 is slid down over sheath 32 until the front end of the charge 48 of hemostatic material reaches artery wall 12.

While slight forward pressure is maintained on the pusher 50 (see arrow A in FIG. 5), inner sheath 32 and sleeve 45 are slowly withdrawn (see arrow B in FIG. 6). As the distal tip 52 of sheath 32 exits from arterial puncture 14 and moves up through sheath 42, the hemostatic material 48 is left exposed to the blood in tissue channel 41, thereby activating the clotting action of the hemostatic material which quickly closes in around the front of sheath 32, sealing puncture 14 and producing hemostasis. Finally, outer sheath 42 can be withdrawn, perhaps with a slight twisting action.

Figure 8:
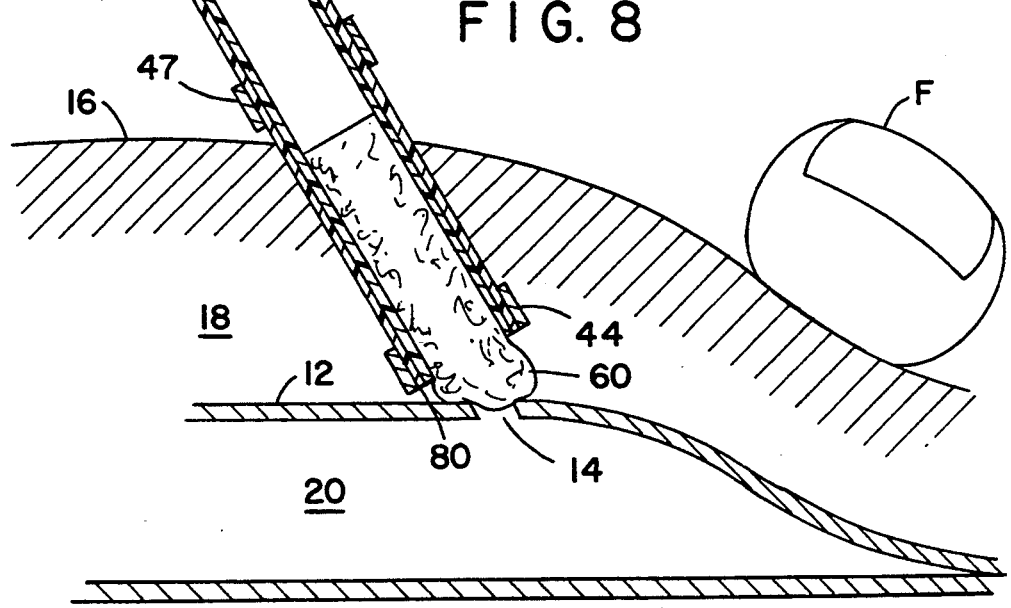
FIG. 8 is a schematic view in section showing both dilators and the inner sheath having been removed and the sleeve of FIG. 7 having been inserted into the outer sheath.

An alternative approach, which is depicted in FIG. 8, is to withdraw both sheath 32 and dilator 36 immediately after completing the medical procedure. If this approach is followed, the physician first clamps the artery (see finger F) upstream of puncture 14 to minimize bleeding. Then a sleeve 54 like that depicted in FIG. 7 is used to insert hemostatic material. Sleeve 54, which is preloaded with hemostatic material 56 is inserted through sheath 42 until the hemostatic material reaches artery wall 12. Sleeve 54 can be provided with a lip 58 at its proximal end. The length of sleeve 54 is such that when lip 58 abuts proximal end 43 of sheath 42, distal tip 60 of sleeve 54 does not pass beyond the distal tip 80 of sheath 42. Alternatively, the physician may rely upon tactile sensation to signal when the hemostatic material has reached wall 12. Sleeve 54 is also provided with a piston 62, a connecting rod 64 and a thumb button 66.

Figure 9:
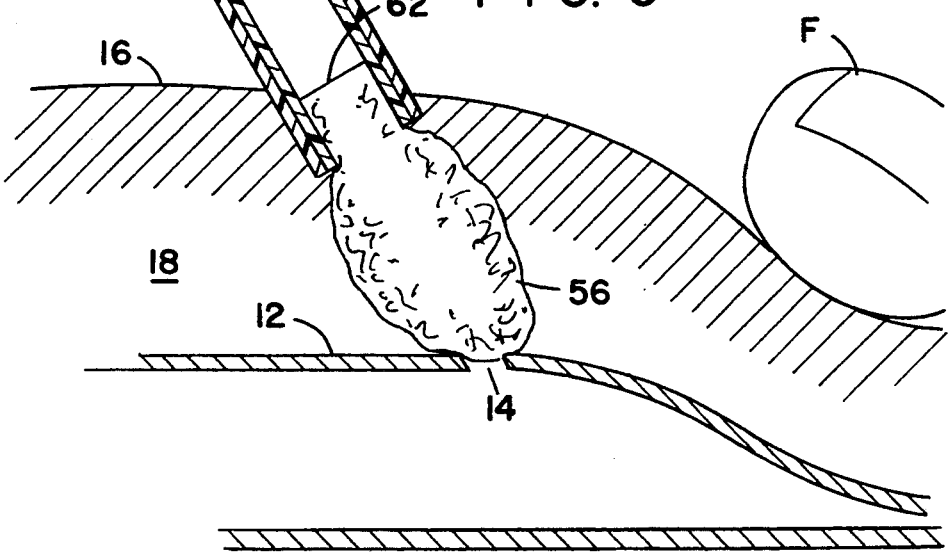
FIG. 9 is a schematic view in section similar to FIG. 6 except that the preloaded sleeve and the outer sheath are being withdrawn while the hemostatic material is held in place.

Slight forward pressure is maintained on button 66 while sleeve 54 is withdrawn (see FIG. 9). Alternatively, sheath 42 can be withdrawn first, followed by sleeve 54 or the two can be withdrawn simultaneously. Irrespective of the sequence, however, as the sleeve is withdrawn, the hemostatic material seals arterial puncture 14 from the outside and produces hemostasis.

As yet another alternative, once the inner sheath 32 and dilator 36 have been removed, leaving only outer sheath 42 in place, a plug of hemostatic material (not shown), preferably preformed but unaided by a sleeve or other confining structure, can be fed directly into sheath 42. Such a preformed plug, because it is larger than puncture 14, will not pass into the arterial lumen but will stop when it reaches wall 12 of artery 10. Once the plug has reached the outside wall of the artery, the outer sheath can be withdrawn. Exposure of the hemostatic material to blood from artery 10 and from the subcutaneous tissue 18 will produce hemostasis.

Although it is not believed to be necessary, any of the above-described alternatives can be practiced with the aid of a guide wire. That guide wire may be the same one used during the medical procedure or it may be a new one inserted specifically for the purpose of assisting in the insertion of the hemostatic material.

Figure 10:
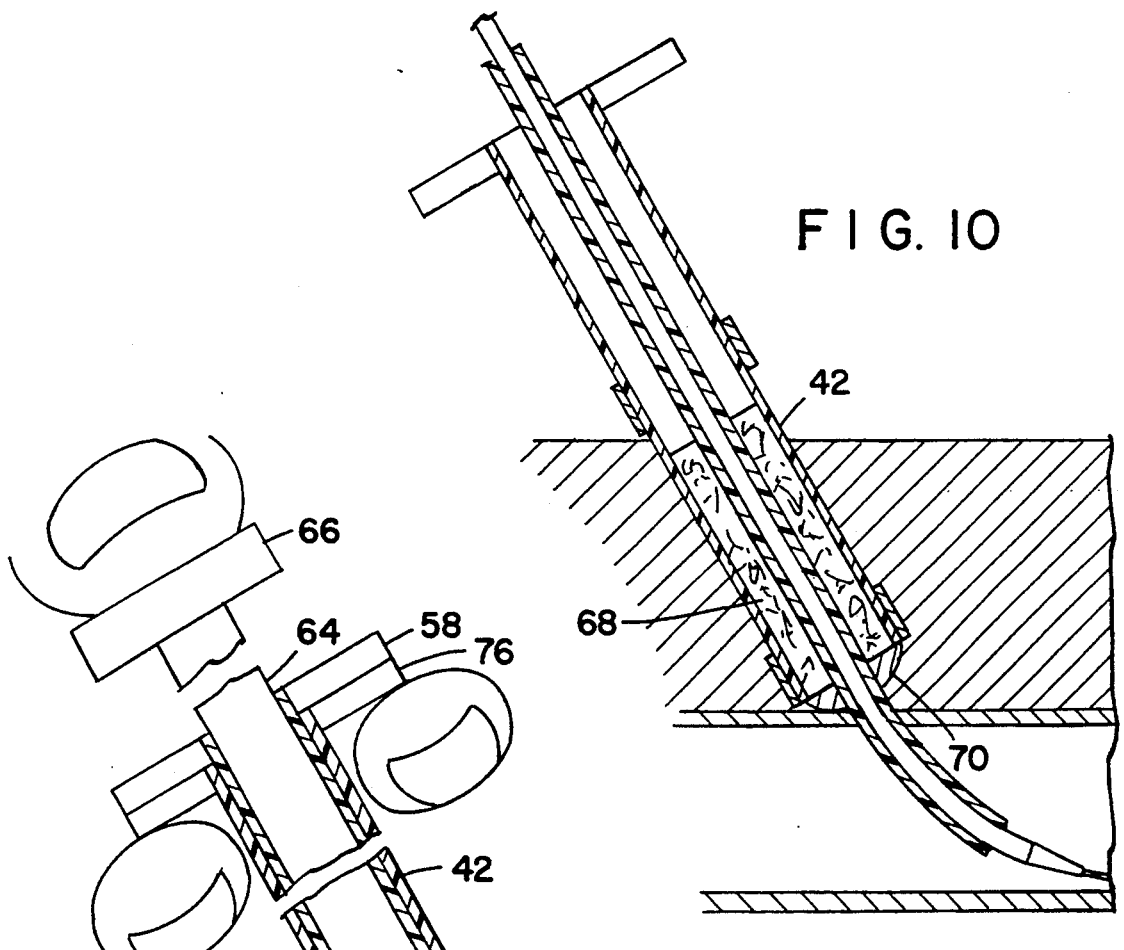
FIG. 10 is a schematic view in section showing hemostatic material preparked in the annular space between the inner and outer sheaths.

The several procedures described above involve insertion of outer sheath 42 at the beginning of the procedure. However, the present invention also contemplates inserting hemostatic material before the medical procedure has been initiated, for use, after the medical procedure has been completed, an approach which may be referred to as preparking. According to this approach as depicted in FIG. 10, once proper placement of sheath 42 and dilator 36 have been confirmed by fluoroscopy, dilator 36 is removed and a charge of hemostatic material 68 is immediately inserted into the annular space vacated by dilator 36. It may also be desirable to reinsert dilator 36 behind hemostatic material 68 or to insert a pusher 50 at this point, but that may be deemed unnecessary. To prevent premature clotting, a flap 70 may be provided at the distal end of either sheath 42 or sheath 32. Alternatively, the front end of plug 68 may be covered with a resorbable membrane (not shown).

Once the hemostatic material is preparked, the physician performs the medical procedure in accordance with standard protocols. After that has been completed and the procedure implements have been removed, the inner sheath can slowly be withdrawn as described above, to expose the hemostatic material to blood from the artery, thereby triggering the clotting action to produce hemostasis.

As still another alternative, before the inner sheath is withdrawn, a new dilator 72 (depicted in FIG. 11) having a long taper 74 is inserted through sheath 32 and into the artery as shown in FIG. 12. Then the inner sheath 32 is removed. Thereafter, dilator 72 is slowly withdrawn. Because taper 74 is so long and narrows so gradually, the hemostatic material around it can close slowly as the taper narrows as shown in FIG. 13. This dilator should most desireably be flexible so as to facilitate passage into the artery. It may be made of polyethylene. The use of a long tapered dilator may be particularly advantageous for use in highly anticoagulated patients. A long taper dilator may be used whether the hemostatic material has been preparked or when it is inserted after the medical procedure has been completed.

Sheath 36 should preferably be made of a biologically compatible material such as TEFLON® and may also be provided with a radiopaque front band 44. The first, or inner sheath 32 should also be made of a biologically compatible material such as TEFLON® or the like.

The two dilators 26 and 36 should also be made of biologically compatible materials such as polyethylene or the like.

As those skilled in the art will readily understand, the sizes of the several components of the present invention will vary depending upon the particular application and the particular medical procedure in connection with which they are to be used. For example, if the PTCA catheter requires a sheath having an 8 Fr. inner lumen (9 Fr. outer lumen), the blunt-nosed outer dilator 36 might have a 9.5 Fr. inner lumen and the outer sheath 42 might have a 14.5 Fr. inner lumen.

What is claimed is:

1. A method of stanching the flow of blood from a patient's wound left after completion of a percutaneous medical procedure wherein said medical procedure is preceded by the insertion of a first sheath from outside the patient's body, through a puncture in the patient's skin, through the underlying tissue and into an artery through an arterial puncture, said method comprising inserting said first sheath from outside the patient's body, through a puncture in the patient's skin, through the underlying tissue and into an artery, passing a sheath-dilator set, comprised of a dilator and a second sheath, each with a front end, over said first sheath, through the patient's skin and through said underling tissue until the front end of said dilator reaches said artery, removing said dilator, leaving an annular space between said first and second sheaths, inserting a charge of hemostatic material into said annular space between said first and second sheaths, after completion of said medical procedure, withdrawing said first sheath from said artery without withdrawing said hemostatic material, permitting said hemostatic material to expand to cover said arterial puncture, withdrawing said second sheath without withdrawing said hemostatic material.

2. The method of claim 1 further comprising the step of maintaining forward pressure on said hemostatic charge while said first sheath is being withdrawn.

3. The method of claim 2 further comprising the step of maintaining forward pressure on said hemostatic charge until hemostasis has been achieved.

4. The method of claim 3 wherein said second sheath is removed after hemostasis has been achieved.

5. The method of claim 1 wherein said hemostatic charge is inserted before said medical procedure is completed.

6. The method of claim 1 wherein said hemostatic charge is inserted after said medical procedure is completed.

7. The method of claim 1 further comprising the steps of inserting a long tapered dilator through said first sheath before withdrawing said first sheath and slowly withdrawing said long tapered dilator after said first sheath has been withdrawn.

* * * * *

UNITED STATES PATENT AND TRADEMARK OFFICE
CERTIFICATE OF CORRECTION

PATENT NO. : 5,437,631
DATED : August 1, 1995
INVENTOR(S) : Ernst Janzen

It is certified that error appears in the above-indentified patent and that said Letters Patent is hereby corrected as shown below:

Title page,
Insert --[30] Foreign Application Priority Data
Sept. 21, 1990 [EP] European Pat. Off.....90118186--.

<u>Column 8,</u>

Line 1, "underling" should read --underlying--.

Signed and Sealed this

Thirtieth Day of January, 1996

Attest:

BRUCE LEHMAN

Attesting Officer

Commissioner of Patents and Trademarks